(12) United States Patent
Macina et al.

(10) Patent No.: US 6,953,658 B2
(45) Date of Patent: Oct. 11, 2005

(54) METHOD OF DIAGNOSING, MONITORING, STAGING, IMAGING AND TREATING GASTROINTESTINAL CANCER

(75) Inventors: Roberto A. Macina, San Jose, CA (US); Alejandra Piderit, Concepcion (CL); Yongmng Sun, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 462 days.

(21) Appl. No.: 09/802,674

(22) Filed: Mar. 9, 2001

(65) Prior Publication Data

US 2002/0042088 A1 Apr. 11, 2002

Related U.S. Application Data

(60) Provisional application No. 60/188,061, filed on Mar. 9, 2000.

(51) Int. Cl.⁷ .............................. C12Q 1/68; C12Q 1/00; G01N 33/567; G01N 33/574; G01N 33/53
(52) U.S. Cl. .............................. 435/6; 435/4; 435/7.21; 435/7.23; 435/7.92; 436/63; 436/64; 436/86; 436/174; 424/9.1; 424/9.2
(58) Field of Search ...................... 424/9.1, 9.2; 435/4, 435/6, 7.21, 7.23, 7.92; 436/63, 64, 174, 86

(56) References Cited

U.S. PATENT DOCUMENTS

| | | | |
|---|---|---|---|
| 4,946,778 A | 8/1990 | Ladner et al. | ............. 435/69.6 |
| 5,580,859 A | 12/1996 | Felgner et al. | ................ 514/44 |
| 5,694,622 A | 12/1997 | Wolff et al. | ................... 514/44 |
| 5,705,151 A | 1/1998 | Dow et al. | ............... 424/93.21 |
| 5,733,478 A | 3/1998 | Yu et al. | .................... 435/70.1 |
| 5,733,748 A | 3/1998 | Yu et al. | .................... 435/70.1 |
| 6,160,090 A | 12/2000 | Schlessinger et al. | |
| 6,337,195 B1 * | 1/2002 | Yu et al. | |
| 2002/0086314 A1 | 7/2002 | Yu et al. | ........................ 435/6 |
| 2002/0160382 A1 | 10/2002 | Lasek et al. | .................... 435/6 |
| 2003/0073105 A1 | 4/2003 | Lasek et al. | .................... 435/6 |
| 2003/0101002 A1 | 5/2003 | Bartha et al. | ................. 702/20 |
| 2003/0109690 A1 * | 6/2003 | Ruben et al. | |

FOREIGN PATENT DOCUMENTS

| | | |
|---|---|---|
| EP | 0841393 A1 | 5/1998 |
| EP | 1 033 401 A3 | 4/2004 |
| WO | WO 90/11092 | 10/1990 |
| WO | WO 96/39419 A1 | 12/1996 |
| WO | WO 96/39419 | 12/1996 |
| WO | WO 96/39541 | 12/1996 |
| WO | WO 97/03190 A1 | 1/1997 |
| WO | WO/98/11779 | 3/1998 |
| WO | WO 98/15624 | 4/1998 |
| WO | WO 98/22139 | 5/1998 |
| WO | WO 00/12702 | 3/2000 |
| WO | WO 00/55351 | 9/2000 |
| WO | WO 01/94629 A2 | 12/2001 |

OTHER PUBLICATIONS

Weeraratna et al. Loss of Uteroglobin Expression in Prostate Cancer: Relationship to Advancing Grade. Clinical Cancer Research 3:2295–2300, Dec. 1997.*
Oka et al. Expression of E–Cadherin Cell Adhesion Molecules in Human Breast Cancer Tissues and Its Relationship to Metastasis. Cancer Research 53:1696–1701, Apr. 1, 1993.*
GenCore Database, Amino acid database. Sequence alignment between Applicants' SEQ ID NO: 4 and sequence 4637 of U.S. Appl No. 20030109690A1 (Jun. 2003).*
GenCore database, nucleic acid comparison between Applicants' SEQ ID NO: 3 and Sequence 17 of U.S. Appl No. 5733748 and 6337195, Mar. 31, 1998 and Jan. 8, 2002.*
Tockman et al. Considerations in Bringing a Cancer Biomarker to Clinical Application. Cancer Research (Suppl.) 52:2711s–2718s, May 1, 1992.*
Abdallah et al., "Non–viral gene transer:Applications in developmental biology and gene therapy", 1995 *Biol. Cell* 85(1):1–7.
Chao et al., "Experimental Kallikrein Gene Therapy in Hypertension, Cardiovascular and Renal Diseases", 1997 *Pharmacol. Res.* 35(6):517–522.
Cooney et al., "Site–Specific Oligonucleotide Binding Represses Transcription of the Human c–*myc* Gene in Vitro", *Science*, 241:456 1988.
Beal and Dervan et al., "Second Structural Motif for Recognition of DNA by Oligonucleotide–Directed Triple–Helix Formation", *Science* 1991 251:1360.
Felgner et al., "Improved Cationic Lipid Formulations *In Vivo* Gene Therapy", 1995 *Ann. NY–Acad. Sci.* 772:126–139.
Griffin et al., "Initial Clinical Study of Indium–111–Labeled Clone 110 Anticarcinoembryonic Antigen Antibody in Patients With Colorectal Cancer", *J. Clin. Onc.* 1991 9:631–640.
Huflejt et al., "Strikingly Different Localization of Galectin–3 and Galectin–4 in Human Colon Adenocarcinoma T84 Cells", *J. Biol. Chem.* 1997 272(22):14294–303.
Kirschmeier et al., "Construction and Characterization of a Retroviral vector Demonstrating Efficient Expression of Cloned cDNA sequences", *DNA* 7:219–25 1988.
Kohler et al., "Continuous cultures of fused cells secreting antibody of predefined specificity", *Nature* 1975 256:495–497.
Kozbor et al., "The production of monoclonal antibodies from human lymphocytes", *Immunology Today* 1983 4:72.
Lauffer R.B.. "Targeted Relaxation Enhancement Agents for MRI*", *Magnetic Resonance in Medicine* 1991 22:339–342.

(Continued)

Primary Examiner—Alana M. Harris
(74) Attorney, Agent, or Firm—Licata & Tyrrell P.C.; Nathan P. Letts

(57) ABSTRACT

The present invention provides new methods and agents for detecting, diagnosing, monitoring, staging, prognosticating, imaging and treating gastrointestinal cancer.

1 Claim, No Drawings

OTHER PUBLICATIONS

Lee et al., "Complexes formed by (pyrimidine)$_n$(purine)$_n$ DNAs on lowering the pH are three–stranded", *Nucleic Acids Res* 1979 6:3073.

Miller et al., "Improved Retroviral Vectors for Gene Transfer and Expression", *Biotechniques* 7:980–990 1989.

Okano et al., "Myelin Basic Protein Gene and the Function of Antisense RNA in Its Repression in Myelin–Deficient Mutant Mouse", *J. Neurochem.* 56: 560 1991.

Proteins Structure and Molecular Properties, 2nd Ed., T. E. Creighton, W. H. Freeman and Company, New York 1993.

Rattan et al., "Aging and Cellular Defense Mechanisms", *Protein Synthesis: Posttranslational Modifications and Aging, Ann. N.Y. Acad. Sci.* 663: 48–62 1992.

Sambrook et al., Molecular Cloning, A Laboratory Manual, 2nd Ed.; Cold Spring Harbor Laboratory Press, Cold Spring Harbor, N.Y. 1989.

Schwartz et al., "Gene transfer by naked DNA into adult mouse brain", 1996 *Gene Ther.* 3(5):405–411.

Sumerdon et al., "An Optimized Antibody–Chelator Conjugate for Imaging of Carcinoembryonic Antigen with Indium–111", *Nucl. Med. Biol.* 1990 17:247–254.

Tabata et al., Arterial gene transfer of acidic fibroblast growth factor for therapeutic angiogenesis in vivo:critical role of secretion signal in use of naked DNA 1997 *Cardiovasc. Res.* 35(3):470–479.

Tsurumi et al., "Direct Intramuscular Gene Transfer of Naked DNA Encoding Vascular Endothelial Growth Factor Augments Collateral Development and Tissue Perfusion"; 1996 *Circulation* 94(12):3281–3290.

Wolff J. A., "Naked DNA transport and expression in mammalian cells", 1997 *Neuromuscul. Disord.* 7(5):314–318.

Hopkins et al., Characterization of the gene encoding carbonic anhydrase I from the pigtail macaque. Gene. 1995; vol. 152:265–269.

Huflejt et al., Strikingly different localization of galectin–3 and galectin–4 in human colon adenocarcinoma T84 cells. JBC. May 30, 1997; vol. 272(22):14294–14303.

Lowe et al., Structure and methylation patterns of the gene encoding human carbonic anhydrase I. Gene. 1990; vol. 93:277–283.

Rechreche et al., Cloning and expression of the mRNA of human galectin–4, an S–type lectin down–regulated in colorectal cancer. Eur. J. Biochem. 1997; vol. 248:22–230.

Database Genebank, Accession No. AB006781, Kato, C., Homo sapiens mRNA for galectin–4, complete cds, Jul. 26 2001, see sequence.

Database Genebank, Accession No. M33987, Lowe, C., Human carbonic anhydrase I (CAI) mRNA, complete cds., Oct. 31, 1994, see sequence.

Bekku et al., "Expression of Carbonic Anhydrase I or II and Correlation to Clinical Aspects of Colorectal Cancer", Hapato–Gastroenterology 2000 47:998–1001.

Brady et al., "The human carbonic anhydrase I gene has two promoters with different tissue specificities", Biochem. J. 1991 277:903–905.

Edwards et al., "Assignment of the gene determining human carbonic anhydrase, CA I, to chromosome 8", Ann. Hum. Genet. 1986 50:123–129.

Gerritsen et al., "In silico data filtering to identify new angiogenesis targets from a large in vitro gene profiling data set", Physiol Genomics 2002 10:13–20.

Kiveläet al., "Differential Expression of Cytoplasmic Carbonic Anhydrases, CA I and II, and Membrane–Associated Isozymes, CA IX and XII, in Normal Mucosa of Large Intestine and in Colorectal Tumors"Digestive Diseases and Sciences 2001 46(10):2179–2186.

Kondo et al., "Estimations of active and inactive carbonic anhydrase isozyme B in human red cells", Clinica Chimica Acta 1975 60:347–353.

Kondo et al., "Estimation and characterization of glycosylated carbonic anhydrase I in erythrocytes from patients with diabetes mellitus", Clinica Chimica Acta 1987 166:227–236.

Kino–Ohsaki et al., "Serum Antibodies to Carbonic Anhydrase I and II in Patients With Idiopathic Chronic Pancreatitis and Sjögren's Syndrome", Gastroenterology 1996 110:1579–1586.

Puscas et al., "The mechanism of action of angiotensin II is dependent on direct activation of vascular smooth muscle carbonic anhydrase I", Int J Clin Lab Res 2000 30:119–125.

Mayeux et al., "Early Postnatal Muscle Contractile Activity Regulates the Carbonic Anhydrase Phenotype of Proprioceptive Neurons in Young and Mature Mice: Evidence for a Critical Period in Development", Neuroscience 1996 72(3):787–795.

Milov et al., "The Effect of Bile Salts on Carbonic Anhydrase", Hepatology 1992 15:288–296.

Mori et al., "The Significance of Carbonic Anhydrase Expression in Human Colorectal Cancer", *Gastroenterology 1993* 105:820–826.

Murakami et al., "Purification and Characterization of Human Salivary Carbonic Anhydrase", J. Biol. Chem. 1987 262(3):1382–1388.

Shepherd et al., "The Measurement of Human Erythrocyte Carbonic Anhydrase I by the Enzyme Linked Immunosorbent Assay (ELISA)", Clin. Biochem. 1982 15(5):248–251.

Siffert et al., "Carbonic anhydrase in human platelets", Biochem. J. 1984 217:727–730.

Sly et al., "Human Carbonic Anhydrases and Carbonic Anhydrase Deficiencies", Annu. Rev. Biochem. 1995 64:375–401.

Venta et al., "Polymorphic gene for human carbonic anhydrase II: A molecular disease marker located on chromosome 8", Proc. Natl. Acad. Sci. USA 1983 80:4437–4440.

Affara et al., "Analysis of chromatin changes associated with the expression of globin and non–globin genes in cell hybrids between erythroid and other cells" Nucleic Acids Research 1985 13(15):5629–5644.

Barlow et al., "Human carbonic anhydrase I cDNA", Nucleic Acids Research 1987 15(5):2386.

Bekku et al., "Carbonic anhydrase I and II as a differentiation marker of human and rat colonic enterocytes", Res Exp Med (Berl). 1998 198(4):175–185.

Chiang et al., "The aberrant expression of cytosolic carbonic anhydrase and its clinical significance in human non–small cell lung cancer", Cancer Lett. 2002 188(1–2):199–205.

Cole et al., "Proteomic analysis of colonic crypts from normal, multiple intestinal neoplasia and p53–null mice:a comparison with colonic polyps", Electrophoresis 2000 21(9):1772–1781.

Curtis P.J., "Cloning of Mouse Carbonic Anhydrase mRNA and Its Induction in Mouse Erythroleukemic Cells", J. Biol. Chem. 1983 258(7):4459–4463.

Collins F.S., "Generation and initial analysis of more than 15,000 full–length human and mouse cDNA sequences", Proc. Natl. Acad. Sci. USA 2002 99(26):16899–16903.

Debili et al., "Expression of platelet glycoproteins by erythroid blasts in four cases of trisomy 21", Leukemia 1989 3(9):669–678.

Dover et al., "Changing erythrocyte populations in juvenile chronic myelocytic leukemia:evidence for disordered regulation", Blood 1977 49(3):355–365.

Ferraroni et al., "Crystal structure of a zinc–activated variant of human carbonic anhydrase I, CA I Michigan 1:evidence for a second zinc binding site involving arginine coordination", Biochemistry 2002 41(20):6237–6244.

Fonti et al., "Carbonic anhydrase I reduction in colonic mucosa of patients wit active ulcerative colitis", Dig Dis Sci 1998 43(9):2086–2092.

Franchi et al., "Carbonic anhydrase inhibitors. Inhibition of cytosolic isozymes I and II and transmembrane, cancer–associated isozyme IX with lipophilic sulfonamides", J. Enzyme Inhib. Med. Chem. 2003 18(4):333–338.

Fraser et al., "The Mouse Carbonic Anhydrase I Gene Contains Two Tissue–Specific Promoters", Molecular and Cellular Biology 1989 9(8):3308–3313.

Frulloni et al., "Elevated Serum Levels of Antibodies to Carbonic Anhydrase I and II in Patients with Chronic Pancreatitis", Pancreas 2000 20(4):382–388.

Gramlich et al., "Immunohistochemical localization of sodium–postassium–stimulated adenosine triphosphatase and carbonic anhydrase in human colon and colonic neoplasms", Arch Pathol Lab Med. 1990 114(4):415–419.

Hori et al., "Effects of thyroid hormone on carbonic anhydrase I gene expression in human erythroid cells", Thyroid 1998 8(6):525–531.

Kikuchi et al., "Effects of thyroid hormone on carbonic anhydrase I levels in human erythroid (YN–1) cells", J Clin Endocrinol Metab 1994 79(1):71–75.

Klade et al., "Identification of tumor antigens in renal cell carcinoma by serological proteome analysis", Proteomics 2001 1(7):890–898.

Kondo et al., "A Novel Low–activity Form of Carbonic Anhydrase I in Erythrocytes of Patients with Primary Aldosteronism", J Biol Chem 1984 259(24):15517–15522.

Kondo et al., "Induction of carbonic anhydrase I isozyme precedes the globin synthesis during erythropoiesis in K562 cells", Am J Hematol 1991 38(3):201–206.

Lönnerholm et al., "Amount and distribution of carbonic anhydrases CA I and CA II in the gastrointestinal tract", Gastroenterology 1985 88(5 Pt 1):1151–1161.

Lowe et al., "Physical mapping of the human carbonic anhyydrase gene cluster on chromosome 8", Genomics 1991 10(4):882–888.

Lowe et al., "Structure and methylation patterns of the gene encoding human carbonic anhydrase I", Gene. 1990 93(2):277–283.

Mitjavila et al., "Effects of granulocyte–macrophage colony–stimulating factor and erythropoietin on leukemic erythroid colony formation in human early erythroblastic leukemias", Blood 1987 70(4):965–973.

Ohata et al., "Acute erythroblastic leukemia presenting as FAB M6 with surface marker positive for megakaryocytic and erythroid:report of a case", Jpn J Clin Hematol 35(2):127–134.

Renes et al., "Epithelial proliferation, cell death, and gene expression in experimental colitis:alterations in carbonic anhydrase I, mucin MUC2, and trefoil factor 3 expression", Int J Colorectal Dis 2002 17(5):317–326.

Shepherd et al., "The Measurement of Human Erythrocyte Carbonic Anhydrase I by the Enzyme Linked Immunosorbent Assay (ELISA)", Clin. Biochem. 1982 15(5):248–251.

Shousha et al., "Distribution of carbonic anhydrase I in gastric and duodenal tissue sections", Arch Pathol Lab Med 1987 111(3):279–281.

Soler et al., "Acute erythroblastic leukemia. Cytological, cytogenetic and phenotypic studies in one case", Acta Haematol 1989 82(2):102–105.

Unwin et al., "Serological and proteomic evaluation of antibody responses in the identification of tumor antigens in renal cell carcinoma", Proteomics 2003 3(1):45–55.

Vaananen H.K., "Immunohistochemical localization of carbonic anhydrase isoenzymes I and II in human bone, cartilage and giant cell tumor", Histochemistry 1984 81(5):485–487.

Wehinger et al., "Myelomonocytic leukemia with Philadelphia–positive and Philadelphia–negative cell lines in early childhood", Klin Wochenschr 1975 53(9):431–436.

Winum et al., "Carbonic anhydrase inhibitors:inhibition of transmembrane, tumor–associated isozyme IX, and cytosolic isozymes I and II with aliphatic sulfamates", J Med Chem 2003 46(25):5471–5477.

NCBI Genbank Accession No. P00915 [gi:115449] Mar. 1, 1992–Oct. 1, 2000 with Revision History.

NCBI Genbank Accession No. P35217 [gi:461679] Feb. 1, 1994–Oct. 1, 2000 with Revision History.

NCBI Genbank Accession No. P00916 [gi:115450] Feb. 1, 1994–Oct. 1, 2000 with Revision History.

NCBI Genbank Accession No. P00917 [gi:115448] Feb. 1, 1994–Oct. 1, 2000 with Revision History.

NCBI Genbank Accession No. P13634 [gi:115451] Feb. 1, 1994–Oct. 1, 2000 with Revision History The revision history for 1345656 which replaces 115451 is provided.

NCBI Genbank Accession No. NM_001738 [gi:4502516] Mar. 19, 1994–Oct. 31, 2000 with Revision History.

NCBI Genbank Accession No. L11622 [gi:177045] Feb. 25, 1993–Dec. 20, 1993 with Revision History.

NCBI Genbank Accession No. AC084734 [gi:11136782] Nov. 10, 2000 with Revision History—The revision history for 21313778 which replaces 11136782 is provided.

NCBI Genbank Accession No. AC008862 [gi:5686211] Aug. 3, 1999–May 5, 2000 with Revision History—the reivsion history of 19774452 which replaces 5686211 is provided.

NCBI Genbank Accession No. X05014 [gi:29599] Aug. 11, 1992–Sep. 12, 1993 with Revision History.

NCBI Genbank Accession No. L25082 [gi:407977] Oct. 13, 1993–Apr. 20, 1995 with Revision History.

NCBI Genbank Accession No. AC025800 [gi:7239686] Mar. 14, 2000–Jan. 26, 2001 with Revision History The revision history of 18767553 which replaces 7239686 is provided.

NCBI Genbank Accession No. M33987 [gi:179792] Sep. 15, 1990–Oct. 31, 1994 with Revision History.

NCBI Genbank Accession No. BC027890 [gi:20380765] May 1, 2002 with Revision History.

Bekku et al., "Expression of Carbonic Anhydrase I or II and Correlation to Clinical Aspects of Colorectal Cancer", Hepato–Gastroenterology 2000 47:998–1001.

* cited by examiner

METHOD OF DIAGNOSING, MONITORING, STAGING, IMAGING AND TREATING GASTROINTESTINAL CANCER

INTRODUCTION

This application claims the benefit of priority from U.S. Provisional Application Ser. No. 60/188,061, filed Mar. 9, 2000.

FIELD OF THE INVENTION

This invention relates, in part, to newly developed assays and compositions for detecting, diagnosing, monitoring, staging, prognosticating, imaging and treating cancers, particularly gastrointestinal cancers including stomach, small intestine and colon cancer.

BACKGROUND OF THE INVENTION

Cancer of the colon is the second most frequently diagnosed malignancy in the United States, as well as the second most common cause of cancer death. Colon cancer is a highly treatable and often curable disease when localized to the bowel. Surgery is the primary treatment and results in cure in approximately 50% of patients. However, recurrence and metastases following surgery is a major problem and often is the ultimate cause of death.

Due to its proximity, cancer of the colon often metastasizes to the small intestine. The prognosis of the cancer spreading to the small intestine is related to the degree of penetration of the tumor through the bowel wall and the presence or absence of nodal involvement. These two characteristics form the basis for all staging systems developed for colon cancer. Various characteristics also assist in prognosticating colon cancer and its spread to the small intestines. For example, bowel obstruction and bowel perforation are indicators of poor prognosis. Elevated pretreatment serum levels of carcinoembryonic antigen (CEA) and of carbohydrate antigen 19-9 (CA 19-9) also have a negative prognostic significance. However, age greater than 70 years at presentation is not a contraindication to standard therapies; acceptable morbidity and mortality, as well as long-term survival, are achieved in this patient population.

Cancer cells can also originate in the small intestine. However, this is a much rarer type of cancer.

Symptoms of cancer of the small intestine typically include pain or cramps in the middle of the abdomen, weight loss without dieting, a lump in the abdomen or blood in the stool.

Cancer of the stomach, also referred to as gastric cancer, also frequently metastasizes to the small intestine due to its proximity. This cancer is often difficult to diagnose in early stages and can be in the stomach for a long time, growing to a large size before symptoms arise. In the early stages of cancer of the stomach, an individual may experience indigestion and stomach discomfort, a bloated feeling after eating, mild nausea, loss of appetite or heartburn. In more advanced stages of stomach cancer, there may be blood in the stool, vomiting, weight loss or more severe pain.

Because of the frequency of these types of cancer (approximately 160,000 new cases of colon and rectal cancer per year alone), the identification of high-risk groups, the demonstrated slow growth of primary lesions and the better survival of early-stage lesions, screening for gastrointestinal cancers should be a part of routine care for all adults starting at age 50, especially those with first-degree relatives with colorectal cancer.

Procedures used for detecting, diagnosing, monitoring, staging, and prognosticating cancer of the colon, small intestine or stomach are of critical importance to the outcome of the patient. Patients diagnosed with early stage cancer generally have a much greater five-year survival rate as compared to the survival rate for patients diagnosed with distant metastasized cancers. New diagnostic methods which are more sensitive and specific for detecting early cancer of the stomach, small intestine and colon are clearly needed.

Patients with gastrointestinal cancers are closely monitored following initial therapy and during adjuvant therapy to determine response to therapy and to detect persistent or recurrent disease of metastasis. There is clearly a need for a cancer marker which is more sensitive and specific in detecting recurrence of these types of cancer.

Another important step in managing gastrointestinal cancers is to determine the stage of the patient's disease. Stage determination has potential prognostic value and provides criteria for designing optimal therapy. Generally, pathological staging of cancer is preferable over clinical staging because the former gives a more accurate prognosis. However, clinical staging would be preferred were it at least as accurate as pathological staging because it does not depend on an invasive procedure to obtain tissue for pathological evaluation. Staging of gastrointestinal cancers would be improved by identifying new markers in cells, tissues, or bodily fluids which could differentiate between different stages of invasion.

Accordingly, there is a great need for more sensitive and accurate methods for the staging of a cancer in a human to determine whether or not such cancer has metastasized and for monitoring the progress of a cancer in a human which has not metastasized for the onset of metastasis.

Thirteen colon specific genes and naturally occurring variants thereof, referred to as CSG1-13, are disclosed in U.S. Pat. No. 5,733,748 and WO 96/39541 for use as diagnostic markers in colon cancer. Some of these genes and polypeptides encoded thereby are also taught to be useful in determining if the colon cancer has metastasized.

It has now been found that galectin-4 and human carbonic anhydrase I serve as useful markers in the diagnosis of gastrointestinal cancer. These diagnostic markers are referred to herein generally as gastrointestinal specific genes or GSGs and more specifically as Cln114 (galectin-4) and Cln115 (human carbonic anhydrase I).

Cln114 was identified as human galectin-4 of 323 amino acids (translated molecular weight of 35918 Dalton). Galectin-4 belongs to the galectin family that include galectin-1 and galectin-3. Both galectin-3 and galectin-4 are found at high concentrations in intestinal extracts. Galectin-4 contains two beta-galactosidase-binding domains and localiazes mainly at sites of cell adhesion. Galectin-4 is a cytosolic protein but like galectin-1 and galectin-3 may be externalized by nonclassical secretory mechanisms and released from the cell. It is possible that galectin-4 is involved in cell adhesion via interaction with extracellular glycoconjugates. Galectin-4 has been suggested to play an important role in the maintenance of epithelial integrity and in the epithelial wound healing process (Huflejt et al. J. Biol. Chem. 1997 272(22):14294–303).

WO098/22139 describes differential expression of galectin-4 in human breast tumor cells. Other members of the galectin superfamily including galectin 8, 9, 10 and 10SV have been described as markers in the diagnosis of cancers including Hodgkin's disease, breast, ovarian, prostate, bone, liver, lung, pancreatic and splenic (see WO 98/15624).

In the present invention, methods are provided for detecting, diagnosing, monitoring, staging, prognosticating, imaging and treating gastrointestinal cancer via the gastrointestinal specific genes referred to herein as GSGs and more specifically as Cln114 and Cln115. For purposes of the present invention, GSG refers, among other things, to native protein expressed by the gene comprising a polynucleotide sequence of SEQ ID NO:1 or 3. Amino acid sequences encoded by the polynucleotides of SEQ ID NO:1 and 3 are depicted in SEQ ID NO:2 and 4, respectively. By "GSG" it is also meant herein polynucleotides which, due to degeneracy in genetic coding, comprise variations in nucleotide sequence as compared to SEQ ID NO:1 or 3, but which still encode the same protein. In the alternative, what is meant by GSG as used herein, means the native mRNA encoded by the gene comprising the polynucleotide sequence of SEQ ID NO:1 or 3, levels of the gene comprising the polynucleotide sequence of SEQ ID NO:1 or 3, or levels of a polynucleotide which is capable of hybridizing under stringent conditions to the antisense sequence of SEQ ID NO:1 or 3.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of gastrointestinal cancer by analyzing for changes in levels of GSG in cells, tissues or bodily fluids compared with levels of GSG in preferably the same cells, tissues, or bodily fluid type of a normal human control, wherein a change in levels of GSG in the patient versus the normal human control is associated with gastrointestinal cancer.

Further provided is a method of diagnosing metastatic gastrointestinal cancer in a patient having gastrointestinal cancer which is not known to have metastasized by identifying a human patient suspected of having gastrointestinal cancer that has metastasized; analyzing a sample of cells, tissues, or bodily fluid from such patient for GSG; comparing the GSG levels in such cells, tissues, or bodily fluid with levels of GSG in preferably the same cells, tissues, or bodily fluid type of a normal human control, wherein a decrease in GSG levels in the patient versus the normal human control is associated with gastrointestinal cancer which has metastasized.

Also provided by the invention is a method of staging gastrointestinal cancer in a human which has such cancer by identifying a human patient having such cancer; analyzing a sample of cells, tissues, or bodily fluid from such patient for GSG; comparing GSG levels in such cells, tissues, or bodily fluid with levels of GSG in preferably the same cells, tissues, or bodily fluid type of a normal human control sample, wherein a decrease in GSG levels in the patient versus the normal human control is associated with a cancer which is progressing and an increase in the levels of GSG is associated with a cancer which is regressing or in remission.

Further provided is a method of monitoring gastrointestinal cancer in a human having such cancer for the onset of metastasis. The method comprises identifying a human patient having such cancer that is not known to have metastasized; periodically analyzing a sample of cells, tissues, or bodily fluids from such patient for GSG; comparing the GSG levels in such cells, tissues, or bodily fluids with levels of GSG in preferably the same cells, tissues, or bodily fluid type of a normal human control sample, wherein a decrease in GSG levels in the patient versus the normal human control is associated with a cancer which has metastasized.

Further provided is a method of monitoring the change in stage of gastrointestinal cancer in a human having such cancer by looking at levels of GSG in a human having such cancer. The method comprises identifying a human patient having such cancer; periodically analyzing a sample of cells, tissues, or bodily fluids from such patient for GSG; comparing the GSG levels in such cells, tissues, or bodily fluids with levels of GSG in preferably the same cells, tissues, or bodily fluid type of a normal human control sample, wherein a decrease in GSG levels in the patient versus the normal human control is associated with a cancer which is progressing and an increase in the levels of GSG is associated with a cancer which is regressing or in remission.

Further provided are methods of designing new therapeutic agents targeted to a GSG for use in imaging and treating gastrointestinal cancer. For example, in one embodiment, therapeutic agents such as antibodies targeted against GSG or fragments of such antibodies can be used to detect or image localization of GSG in a patient for the purpose of detecting or diagnosing a disease or condition. In this embodiment, a decrease in the amount of labeled antibody detected as compared to normal tissue would be indicative of tumor metastases or growth. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. Therapeutic agents such as small molecules or antibodies which increase the concentration and/or activity of GSGs can also be used in the treatment of diseases characterized by underexpression of GSG. Such agents can be readily identified in accordance with the teachings herein.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

GLOSSARY

The following illustrative explanations are provided to facilitate understanding of certain terms used frequently herein. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 µg of plasmid or DNA fragment is digested with about 2 units of enzyme in about 20 µl of reaction buffer. For the purpose of isolating DNA fragments for plasmid construction, typically 5 to 50 µg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. When introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides. Often the term refers to single-stranded deoxyribonucleotides, but it can refer as well to single- or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case "p" preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in voluminous research literature, and they are well known to those of skill in the art.

Known modifications which may be present in polypeptides of the present invention include, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing events and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same post-translational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

A variant may comprise a polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

A variant may also comprise a polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with GSG polypeptides of the present invention and is inclusive not only of classic receptors, which are preferred, but also other molecules that specifically bind to or interact with polypeptides of the invention (which also may be referred to as "binding molecules" and "interaction molecules," respectively and as "GSG binding or interaction molecules", "Cln114 and Cln115 binding molecules" and "Cln114 and Cln115 interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind to polypeptides of the invention.

DETAILED DESCRIPTION OF THE INVENTION

The present invention relates to diagnostic assays and methods, both quantitative and qualitative for detecting, diagnosing, monitoring, staging and prognosticating cancers by comparing levels of GSG in a human patient with those of GSG in a normal human control. The present invention also relates to agents and methods for identifying and using agents which modulate GSG activity and/or levels to treat diseases or disorders associated with decreased levels of GSG. For purposes of the present invention, what is meant by GSG levels is, among other things, native protein expressed by the gene comprising a polynucleotide sequence of SEQ ID NO: 1 or 3. Amino acid sequences encoded by the polynucleotide sequences of SEQ ID NO:1 and 3 are depicted in SEQ ID NO:2 and 4, respectively. By "GSG" it is also meant herein polynucleotides which, due to degeneracy in genetic coding, comprise variations in nucleotide sequence as compared to SEQ ID NO:1 or 3, but which still encode the same protein. The native protein being detected may be whole, a breakdown product, a complex of molecules or chemically modified. In the alternative, what is meant by GSG as used herein, means the native mRNA encoded by the gene comprising the polynucleotide sequence of SEQ ID NO: 1 or 3, levels of the gene comprising the polynucleotide sequence of SEQ ID NO: 1 or 3, or levels of a polynucleotide which is capable of hybridizing under stringent conditions to the antisense sequence of SEQ ID NO: 1 or 3. Such levels are preferably determined in at least one of cells, tissues and/or bodily fluids, including determination of normal and abnormal levels. Thus, for instance, a diagnostic assay in accordance with the invention for diagnosing underexpression of GSG protein compared to normal control bodily fluids, cells, or tissue samples may be used to diagnose the presence of gastrointestinal cancer.

All the methods of the present invention may optionally include determining the levels of other cancer markers as well as GSG. Other cancer markers, in addition to GSG, useful in the present invention will depend on the cancer being tested and are known to those of skill in the art.

Diagnostic Assays

The present invention provides methods for diagnosing the presence of cancer, and in particular gastrointestinal cancer including stomach, small intestine and colon cancer, by analyzing for changes in levels of GSG in cells, tissues or bodily fluids compared with levels of GSG in cells, tissues or bodily fluids of preferably the same type from a normal human control, wherein a decrease in levels of GSG in the patient versus the normal human control is associated with the presence of gastrointestinal cancer.

Without limiting the instant invention, typically, for a quantitative diagnostic assay a positive result indicating the patient being tested has cancer is one in which cells, tissues or bodily fluid levels of the cancer marker, such as GSG, are at least two times lower, and most preferably are at least five times lower, than in preferably the same cells, tissues or bodily fluid of a normal human control.

The present invention also provides a method of diagnosing metastatic gastrointestinal cancer in a patient having gastrointestinal cancer which has not yet metastasized for the onset of metastasis. In the method of the present invention, a human cancer patient suspected of having gastrointestinal cancer which may have metastasized (but which was not previously known to have metastasized) is identified. This is accomplished by a variety of means known to those of skill in the art.

In the present invention, determining the presence of GSG levels in cells, tissues or bodily fluid, is particularly useful for discriminating between gastrointestinal cancer which has not metastasized and gastrointestinal cancer which has metastasized. Existing techniques have difficulty discriminating between gastrointestinal cancer which has metastasized and gastrointestinal cancer which has not metastasized and proper treatment selection is often dependent upon such knowledge.

In the present invention, the cancer marker levels measured in such cells, tissues or bodily fluid is GSG, and are compared with levels of GSG in preferably the same cells, tissues or bodily fluid type of a normal human control. That is, if the cancer marker being observed is GSG in serum, this level is preferably compared with the level of GSG in serum of a normal human control. A decrease in the GSG in the patient versus the normal human control is associated with gastrointestinal cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as GSG, are at least two times lower, and most preferably are at least five times lower, than in preferably the same cells, tissues or bodily fluid of a normal patient.

Normal human control as used herein includes a human patient without cancer and/or non cancerous samples from the patient; in the methods for diagnosing or monitoring for metastasis, normal human control may preferably also include samples from a human patient that is determined by reliable methods to have gastrointestinal cancer which has not metastasized.

Staging

The invention also provides a method of staging gastrointestinal cancer in a human patient. The method comprises identifying a human patient having such cancer and analyzing cells, tissues or bodily fluid from such human patient for GSG. The GSG levels determined in the patient are then compared with levels of GSG in preferably the same cells, tissues or bodily fluid type of a normal human control, wherein a decrease in GSG levels in the human patient versus the normal human control is associated with a cancer which is progressing and an increase in the levels of GSG (but still decreased over true normal levels) is associated with a cancer which is regressing or in remission.

Monitoring

Further provided is a method of monitoring gastrointestinal cancer in a human patient having such cancer for the onset of metastasis. The method comprises identifying a human patient having such cancer that is not known to have metastasized; periodically analyzing cells, tissues or bodily fluid from such human patient for GSG; and comparing the GSG levels determined in the human patient with levels of GSG in preferably the same cells, tissues or bodily fluid type of a normal human control, wherein a decrease in GSG levels in the human patient versus the normal human control is associated with a cancer which has metastasized. In this method, normal human control samples may also include prior patient samples.

Further provided by this invention is a method of monitoring the change in stage of gastrointestinal cancer in a human patient having such cancer. The method comprises identifying a human patient having such cancer; periodically analyzing cells, tissues or bodily fluid from such human patient for GSG; and comparing the GSG levels determined in the human patient with levels of GSG in preferably the same cells, tissues or bodily fluid type of a normal human control, wherein a decrease in GSG levels in the human patient versus the normal human control is associated with a cancer which is progressing in stage and an increase in the levels of GSG is associated with a cancer which is regressing in stage or in remission. In this method, normal human control samples may also include prior patient samples.

Monitoring a patient for onset of metastasis is periodic and preferably done on a quarterly basis. However, this may be done more or less frequently depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with decreased levels of GSG. The present invention provides a method in which a test sample is obtained from a human patient and GSG is detected. The presence of lower GSG levels as compared to normal human controls is diagnostic for the human patient being at risk for developing cancer, particularly gastrointestinal cancer.

The effectiveness of therapeutic agents to increase expression or activity of the GSGs of the invention can also be monitored by analyzing levels of expression of the GSGs in a human patient in clinical trials or in in vitro screening assays such as in human cells. In this way, the gene expression pattern can serve as a marker, indicative of the physiological response of the human patient, or cells as the case may be, to the agent being tested.

Detection of Genetic Lesions or Mutations

The methods of the present invention can also be used to detect genetic lesions or mutations in GSG, thereby determining if a human with the genetic lesion is at risk for gastrointestinal cancer or has gastrointestinal cancer. Genetic lesions can be detected, for example, by ascertaining the existence of a deletion and/or addition and/or substitution of one or more nucleotides from the GSGs of this invention, a chromosomal rearrangement of GSG, aberrant modification of GSG (such as of the methylation pattern of the genomic DNA), the presence of a non-wild type splicing pattern of a mRNA transcript of GSG, allelic loss of GSG, and/or inappropriate post-translational modification of GSG protein. Methods to detect such lesions in the GSG of this invention are known to those of skill in the art.

Assay Techniques

Assay techniques that can be used to determine levels of gene expression (including protein levels), such as GSG of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches: two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to GSG, preferably a monoclonal antibody. In addition a reporter antibody generally is prepared which binds specifically to GSG. The reporter antibody is attached to a detectable reagent such as radioactive, fluorescent or enzymatic reagent, for example horseradish peroxidase enzyme or alkaline phosphatase.

To carry out the ELISA, antibody specific to GSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time GSG binds to the specific antibody attached to the polystyrene dish. Unbound sample is washed out with buffer. A reporter antibody specifically directed to GSG and linked to a detectable reagent such as horseradish peroxidase is placed in the dish resulting in binding of the reporter antibody to any monoclonal antibody bound to GSG. Unattached reporter antibody is then washed out. Reagents for peroxidase activity, including a calorimetric substrate are then added to the dish. Immobilized peroxidase, linked to GSG antibodies, produces a colored reaction product. The amount of color developed in a given time period is proportional to the amount of GSG polypeptide present in the sample. Quantitative results typically are obtained by reference to a standard curve.

A competition assay can also be employed wherein antibodies specific to GSG are attached to a solid support and labeled GSG and a sample derived from the host are passed over the solid support. The amount of label detected which is attached to the solid support can be correlated to a quantity of GSG in the sample.

Using all or a portion of a nucleic acid sequence of GSG of the present invention as a hybridization probe, nucleic acid methods can also be used to detect GSG mRNA as a marker for gastrointestinal cancer. Polymerase chain reaction (PCR) and other nucleic acid methods, such as ligase chain reaction (LCR) and nucleic acid sequence based amplification (NASBA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to both detect the expression of and quantitate the level of expression of that gene. In this approach, a cDNA encoding the GSG gene is fixed to a substrate. The substrate may be of any suitable type including but not limited to glass, nitrocellulose, nylon or plastic. At least a portion of the DNA encoding the GSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood.

In Vivo Targeting of GSG/Monitoring and Treating Gastrointestinal Cancer Therapy Identification of these GSGs is also useful in the rational design of new therapeutics for imaging and monitoring cancer treatment, and in particular gastrointestinal cancer treatment. For example, in one embodiment, antibodies which specifically bind to GSG can be raised and used in vivo in patients suffering from gastrointestinal cancer to monitor decreases or increases in GSG levels indicative of the efficacy of the treatment and/or the spreading of the cancer. Antibodies which specifically bind GSG can be injected into a patient having gastrointestinal cancer for diagnostic and/or therapeutic purposes. Thus, another aspect of the present invention provides for a method for monitoring treatment of gastrointestinal cancer in a human patient by administering to the patient a GSG antibody.

The preparation and use of antibodies for in vivo diagnosis and treatment is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against GSG can be used in a similar manner. Labeled antibodies which specifically bind GSG can be injected into patients suspected of having gastrointestinal cancer for the purpose of diagnosing or staging of the disease status of the patient. The label used will be selected in accordance with the imaging modality to be used. For example, radioactive labels such as Indium-111, Technetium-99 m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Presence or absence of the label, as compared to imaging of normal tissue, permits determination of the spread of the cancer. The amount of label within an organ or tissue also allows determination of the presence or absence of cancer in that organ or tissue.

Antibodies which can be used in in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Small molecules predicted via computer imaging to specifically bind to regions of GSG can also be designed, synthesized and tested for use in the imaging and treatment of gastrointestinal cancer. Further, libraries of molecules can be screened for potential anticancer agents by assessing the ability of the molecule to bind to the GSGs identified herein. Molecules identified in the library as being capable of binding to GSG are key candidates for further evaluation for use in the treatment of gastrointestinal cancer. In a preferred embodiment, these molecules will upregulate expression and/or activity of GSG in cells.

Antibodies

GSG polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, techniques which provide antibodies produced by continuous cell line cultures can be used. Examples include the hybridoma technique (Kohler, G. and Milstein, C., Nature 256: 495–497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Using "Peptide Structure" analysis in GCG, the following potential antigenic epitopes have been identified:

| | | |
|---|---|---|
| $Pro^7$-$Pro^{22}$ | PAPGYQPTYNPTLPYYQP | (SEQ ID NO:5) |
| $Pro^{66}$-$Arg^{91}$ | PRFDGWDKVVFNTLQGGKWGSEER KR | (SEQ ID NO:6) |
| $Pro^{154}$-$Asn^{177}$ | PLRPQGPPMMPPYPGPGHCHQQLN | (SEQ ID NO:7) |
| $Trp^{256}$-$Pro^{270}$ | WGSEEKKITHNPFGP | (SEQ ID NO:8) |

Screening Assays

The present invention also provides methods for identifying modulators which bind to GSG polypeptides or have a modulatory effect on the expression or activity of GSG polypeptides. Modulators which increase the expression or activity of GSG polypeptides are believed to be useful in treating gastrointestinal cancer. Such screening assays are known to those of skill in the art and include, without limitation, cell-based assays and cell free assays.

For example, genes encoding proteins that bind GSGs, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991). Expression cloning can also be employed for this purpose. To this end, polyadenylated RNA is prepared from a cell responsive to a GSG of the present invention; a cDNA library is created from this RNA; the library is divided into pools; and the pools are transfected individually into cells that are not responsive to the GSG. The transfected cells then are exposed to labeled GSG. The GSGs of the present invention can be labeled by a variety of well-known techniques including standard methods of radio-iodination or inclusion of a recognition site for a site-specific protein kinase. Following exposure, the cells are fixed and binding of cytostatin is determined. In a preferred embodiment, these procedures are carried out on glass slides. Pools of cDNA that produce GSG-binding cells are then identified. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity-linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

GSG polypeptides of the invention also can be used to assess binding capacity of GSG binding molecules, such as receptor molecules, in cells or in cell-free preparations.

The invention also provides methods of screening compounds to identify those which enhance or block the action of GSGs on cells, such as its interaction with GSG-binding molecules such as receptor molecules. An agonist is a compound which increases the natural biological functions of GSGs of the present invention or which functions in a manner similar to the GSGs, while antagonists decrease or eliminate such functions.

In one embodiment of an agonist/antagonist screening assay, a cellular compartment, such as a membrane or a preparation thereof, such as a membrane-preparation, is prepared from a cell that expresses a molecule that binds a GSG of the present invention, such as a molecule of a signaling or regulatory pathway modulated by GSG. The preparation is incubated with labeled GSG in the absence or the presence of a candidate molecule which may be a GSG agonist or antagonist. The ability of the candidate molecule to bind the binding molecule is reflected in decreased binding of the labeled ligand. Molecules that bind well and elicit effects that are the same as or closely related to the GSGs are agonists. Molecules that bind well but do not elicit such effects are likely to be antagonists. GSG-like effects of potential agonists and antagonists may by measured, for instance, by determining activity of a second messenger system following interaction of the candidate molecule with a cell or appropriate cell preparation, and comparing the effect with that of GSGs or molecules that elicit the same effects as GSGs. Second messenger systems that may be useful in this regard include, but are not limited to, AMP guanylate cyclase, ion channel or phosphoinositide hydrolysis second messenger systems.

Another example of an assay for GSG antagonists is a competitive assay that combines a GSG of the present invention and a potential antagonist with membrane-bound GSG receptor molecules or recombinant GSG receptor molecules under appropriate conditions for a competitive inhibition assay. GSGs can be labeled, such as by radioactivity, such that the number of GSG molecules bound to a receptor molecule can be determined accurately to assess the effectiveness of the potential antagonist.

Potential agonists include small organic molecules, peptides, polypeptides and antibodies that mimic binding of a GSG polypeptide to its receptor, thereby enhancing its activity. Potential agonists also include agents which increase expression of GSGs.

Potential antagonists also may be small organic molecules, a peptide, a polypeptide such as a closely related protein or antibody that binds the same sites on a binding molecule, such as a receptor molecule, without inducing GSG-induced activities, thereby preventing the action of GSGs by excluding GSGs from binding. Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing GSG-induced activities, thereby preventing the action of GSGs by excluding GSGs from binding. Potential antagonists include small molecules which bind to and occupy the binding site of the GSG polypeptides thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of GSGs of the present invention. The antisense RNA oligonucleotide hybridizes to the mRNA in vivo and blocks translation of the mRNA molecule into a GSG polypeptide. The oligonucleotides described above can also be delivered to cells such that the antisense RNA or DNA may be expressed in vivo to inhibit production of GSGs.

Compositions for Treatment of GSG Related Diseases

It will be appreciated that conditions caused by a decrease in the standard or normal expression level of a GSG in an individual can be treated by administering a GSG of the present invention, preferably in the secreted form, or an agonist of GSG. Thus, the invention also provides a method of treatment of an individual in need of an increased level of the polypeptide comprising administering to such an individual a pharmaceutical composition comprising an amount of a GSG polypeptide or agonist to increase the activity level of the GSG polypeptide in such an individual.

Thus, the present invention also relates to compositions comprising a GSG polypeptide or agonist. These polypeptides or agonists may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 $\mu$g/kg body weight per day. Preferably, in most cases, dose is from about 10 $\mu$g/kg to about 2 $\mu$g/kg body weight, daily. It will be appreciated that optimum dosage will be determined by standard methods for each treatment modality and indication, taking into account the indication, its severity, route of administration, complicating conditions and the like.

The invention further relates to pharmaceutical packs and kits comprising one or more containers filled with one or more of the polypeptides or other compounds of the present invention. Associated with such container(s) can be a notice in the form prescribed by a governmental agency regulating the manufacture, use or sale of pharmaceuticals or biological products, reflecting approval by the agency of the manufacture, use or sale of the product for human administration.

Gene Therapy

The GSG polynucleotides, polypeptides, agonists and antagonists that are polypeptides may be employed in accordance with the present invention by expression of such polypeptides in vivo, in treatment modalities often referred to as "gene therapy." Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and .beta.-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding s polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter; the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the beta-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19–14X, VT-19-17-H2, YCRE, YCRIP, GP+E-86, GP+envAml2, and DAN cell lines as described in Miller, A., Human Gene Therapy 1: 5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted so that the chunks of tissue remain fixed to the bottom of the flask and fresh media (e. g., Ham's F12 media, with 10% FBS, penicillin and streptomycin) is added. The flasks are then incubated at 37° C. for approximately one week. At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7: 219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+aml2 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media.

If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Gene therapy methods can be used in vivo to treat disorders, diseases and conditions relating to underexpression of a GSG of the present invention. The gene therapy method relates to the introduction of naked nucleic acid (DNA, RNA, and antisense DNA or RNA) sequences into an animal to increase or decrease the expression of the polypeptide.

The polynucleotide of the present invention may be operatively linked to a promoter or any other genetic elements necessary for the expression of the polypeptide by the target tissue. Such gene therapy and delivery techniques and methods are known in the art, see, for example, WO 90/11092, WO 98/11779; U. S. Pat. Nos. 5,693,622; 5,705,151; 5,580,859; Tabata H. et al. (1997) Cardiovasc. Res. 35 (3): 470–479, Chao J et al. (1997) Pharmacol. Res. 35 (6): 517–522, Wolff J. A. (1997) Neuromuscul. Disord. 7 (5): 314–318, Schwartz B. et al. (1996) Gene Ther. 3 (5): 405–411, Tsurumi Y. et al. (1996) Circulation 94 (12): 3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772: 126–139 and Abdallah B. et al. (1995) Biol. Cell 85 (1): 1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within an animal, including that of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 $\mu$g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice.

The results of the above experimentation in mice can be use to extrapolate proper dosages and other treatment parameters in humans and other animals using naked DNA.

EXAMPLES

The present invention is further described by the following examples. These examples are provided solely to illustrate the invention by reference to specific embodiments. These exemplifications, while illustrating certain aspects of the invention, do not portray the limitations or circumscribe the scope of the disclosed invention.

All examples outlined here were carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 1

Relative Quantitation of Gene Expression

Real-Time quantitative PCR with fluorescent Taqman probes is a quantitation detection system utilizing the 5'–3' nuclease activity of Taq DNA polymerase. The method uses an internal fluorescent oligonucleotide probe (Taqman) labeled with a 5' reporter dye and a downstream, 3' quencher dye. During PCR, the 5'–3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH), ATPsy6 (ATP synthase 6), or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene were evaluated for every sample in normal and cancer tissues. Total RNA was extracted from normal tissues, cancer tissues, and from cancers and the corresponding matched adjacent tissues. Subsequently, first strand cDNA was prepared with reverse transcriptase and the polymerase chain reaction was done using primers and Taqman probes specific to each target gene. The results were analyzed using the ABI PRISM 7700 Sequence Detector. The absolute numbers are relative levels of expression of the target gene in a particular tissue compared to the calibrator tissue.
Expression of Cln114; Gene ID2385453 (Human Galectin-4):

For the GSG Cln114, real-time quantitative PCR was performed using the following primers:
Forward Primer:
5'-AACCCGCCTGTGCCATATT-3' (SEQ ID NO:9)
Reverse Primer
5'-GGAGCCCACCTTGAAGTTGATA-3' (SEQ ID NO:10)

The absolute numbers depicted in Table 1 are relative levels of expression of the GSG referred to as Cln114 in 12 normal different tissues. All the values are compared to normal uterus (calibrator). These RNA samples are commercially available pools, originated by pooling samples of a particular tissue from different individuals.

TABLE 1

Relative Levels of GSG Cln114 Expression in Pooled Samples

| TISSUE | NORMAL |
|---|---|
| Colon-Ascending | 6562.4 |
| Endometrium | 1.4 |
| Kidney | 0.4 |
| Liver | 3.9 |
| Ovary | 9.5 |
| Pancreas | 9.6 |
| Prostate | 1.0 |
| Small Intestine | 213.8 |
| Spleen | 4.5 |
| Stomach | 59.3 |
| Testis | 1.7 |
| Uterus | 1.0 |

The relative levels of expression in Table 1 show that Cln114 mRNA expression is more than 30 fold higher in the pool of normal ascending colon (6562.4) compared with small intestine (213.8), and more than 110 fold higher than the expression in stomach (59.3). The other tissues tested show expression levels 650 fold lower than the levels in colon. These results demonstrate that Cln114 mRNA expression is highly specific for gastrointestinal tissues including the colon, small intestine, and stomach.

The absolute numbers in Table 1 were obtained analyzing pools of samples of a particular tissue from different individuals. They can not be compared to the absolute numbers originated from RNA obtained from tissue samples of a single individual in Table 2.

The absolute numbers depicted in Table 2 are relative levels of expression of Cln114 in 45 pairs of matching samples. All the values are compared to normal uterus (calibrator). A matching pair is formed by mRNA from the cancer sample for a particular tissue and mRNA from the normal adjacent sample for that same tissue from the same individual.

TABLE 2

Relative Levels of GSG Cln114 Expression in Individual Samples

| SAMPLE ID | TISSUE | CANCER | MATCHING NORMAL ADJACENT |
|---|---|---|---|
| StoMT54 | Stomach 1 | 290.4 | 201.6 |
| SmI21XA | Small Intestine 1 | 842.4 | 379.8 |
| ClnAS45 | Colon-Ascending(A)1 | 652.6 | 2215.3 |
| ClnCM67 | Colon-Cecum(B)2 | 637.7 | 2072.3 |
| ClnAS67 | Colon-Ascending(B)3 | 657.1 | 566.1 |
| ClnAS12 | Colon-Ascending(B)4 | 503.4 | 4793.4 |
| ClnAS43 | Colon-Ascending(C)5 | 9878.2 | 3108.8 |
| ClnAS46 | Colon-Ascending(C)6 | 5097.5 | 9543.6 |
| ClnAS89 | Colon-Ascending(D)7 | 491.1 | 129.8 |
| ClnAC19 | Colon-Ascending(D)8 | 1003.8 | 3694.2 |
| ClnTX01 | Colon-Transverse(B)9 | 723.1 | 2278.4 |
| ClnTX89 | Colon-Transverse(B)10 | 1337.2 | 464.6 |
| ClnTX67 | Colon-Transverse(C)11 | 989.1 | 1205.2 |
| ClnSG27 | Colon-Sigmoid(C)12 | 1738.1 | 2833.0 |
| ClnSG20 | Colon-Sigmoid(B)13 | 870.1 | 2370.0 |
| ClnSG45 | Colon-Sigmoid(D)14 | 754.8 | 1067.5 |
| ClnB34 | Colon-Rectosigmoid(A)15 | 562.2 | 664.0 |
| ClnCXGA | Colon-Rectum(A)16 | 2486.7 | 3327.7 |
| ClnRC67 | Colon-Rectum(B)17 | 164.8 | 1132.3 |
| ClnC9XR | Colon-Rectosigmoid(D)18 | 851.5 | 1883.4 |
| ClnRC01 | Colon-Rectum(C)19 | 1652.0 | 343.7 |
| ClnRC89 | Colon-Rectum(D)20 | 5.0 | 2556.6 |
| Bld32XK | Bladder 1 | 0.5 | 9.3 |
| Bld46XK | Bladder 2 | 0.5 | 0.8 |
| CvxKS83 | Cervix 1 | 0.6 | 4.8 |
| CvxKS52 | Cervix 2 | 1.5 | 2.4 |
| End12XA | Endometrium 1 | 0.5 | 7.3 |
| Kid11XD | Kidney 1 | 8.5 | 0.2 |
| Kid10XD | Kidney 2 | 14.4 | 1.7 |
| Kid107XD | Kidney 3 | 20.2 | 0.7 |
| Kid109XD | Kidney 4 | 849.3 | 4.9 |
| Kid106XD | Kidney 5 | 0.1 | 2.9 |
| Liv42X | Liver 1 | 270.0 | 5.0 |
| Liv15XA | Liver 2 | 41.7 | 14.4 |
| Liv94XA | Liver 3 | 19.3 | 2.0 |

TABLE 2-continued

Relative Levels of GSG Cln114 Expression in Individual Samples

| SAMPLE ID | TISSUE | CANCER | MATCHING NORMAL ADJACENT |
|---|---|---|---|
| Lng90X | Lung 1 | 1.5 | 1.2 |
| Lng60XL | Lung 2 | 1.6 | 1.8 |
| LngAC11 | Lung 3 | 12.1 | 2.8 |
| Lng47XQ | Lung 4 | 0.5 | 2.0 |
| Mam14DN | Mammary Gland 1 | 2.3 | 0.0 |
| Mam12X | Mammary Gland 2 | 0.0 | 0.0 |
| Pro12B | Prostate 1 | 2.1 | 0.2 |
| Tst39X | Testis 1 | 45.5 | 2.0 |
| Utr85XU | Uterus 1 | 0.7 | 1.6 |
| Utr135XO | Uterus 2 | 0.5 | 0.2 |

0 = Negative

In the analysis of matching samples, the higher levels of expression were in colon, stomach, and small intestine, showing a high degree of tissue specificity. High levels of mRNA for Cln114 were seen in only one sample out of five matching samples for kidney (the cancer sample for the matching sample kidney #4 with a relative expression of 849.3). Also one sample out of three matching samples for liver (the cancer sample for the matching sample liver #1 with 270.0) showed high levels of mRNA for Cln114. These results confirm the tissue specificity results obtained with the panel of normal pooled samples (Table 1).

Furthermore, the level of mRNA expression in cancer samples and the isogenic normal adjacent tissue from the same individual were compared. This comparison provides an indication of specificity for the cancer stage (e.g. different levels of mRNA expression in the cancer sample compared to the normal adjacent). Table 2 shows lower expression of Cln114 in 15 colon cancer tissues (out of 20) compared with their respective normal adjacent (colon samples #1, 2, 4, 6, 8, 9, 11, 12, 13, 14, 15, 16, 17, 18, and 20). There was underexpression in the cancer tissue for 75% of the colon matching samples tested (15 out of 20 total colon matching samples). The matching samples stomach #1 (sto MT54) and small intestine #1 (SmI 21XA) showed upregulation of mRNA for Cln114 in the cancer sample. After establishing a normal value for healthy individuals, lower levels of the product encoded by the gene Cln114 could have diagnostic value for colon cancer, detecting close to 75% of the cases tested.

Altogether, the high level of tissue specificity, plus the lower mRNA expression in 75% of the colon matching samples tested are indicative of Cln114 being a diagnostic marker for gastrointestinal cancer, specifically for stomach, small intestine, and colon cancer.

Expression of Gene ID 179792 (Cln115):

For the GSG Cln115, real-time quantitative PCR was performed using the following primers:

Forward Primer

5'-GGCTGATGGTTTGGCAGTTA-3' (SEQ ID NO:11)

Reverse Primer

5'-TTGTGAATGGGGCTCGTTT-3' (SEQ ID NO:12)

The absolute numbers depicted in Table 3 are relative levels of expression of the GSG Cln115 in 12 normal different tissues. All the values are compared to normal ovary (calibrator). These RNA samples are commercially available pools, originated by pooling samples of a particular tissue from different individuals.

TABLE 3

Relative Levels of GSG Cln115 Expression in Pooled Samples

| TISSUE | NORMAL |
|---|---|
| Colon-Ascending | 1052.8 |
| Endometrium | 0.04 |
| Kidney | 0.1 |
| Liver | 0.03 |
| Ovary | 1.0 |
| Pancreas | 0 |
| Prostate | 0.1 |
| Small Intestine | 0.01 |
| Spleen | 1.6 |
| Stomach | 0.1 |
| Testis | 0.2 |
| Uterus | 0.2 |

The relative levels of expression in Table 3 show that Cln115 mRNA expression is more than 1000 fold higher in the pool of normal ascending colon (1052.8) compared to any other tissue tested. These results demonstrate that Cln115 mRNA expression is highly specific for colon.

The absolute numbers in Table 3 were obtained analyzing pools of samples of a particular tissue from different individuals. They can not be compared to the absolute numbers originated from RNA obtained from tissue samples of a single individual in Table 4.

The absolute numbers depicted in Table 4 are relative levels of expression of Cln115 in 51 pairs of matching samples. All the values are compared to normal ovary (calibrator). A matching pair is formed by mRNA from the cancer sample for a particular tissue and mRNA from the normal adjacent sample for that same tissue from the same individual.

TABLE 4

Relative Levels of GSG Cln115 Expression in Individual Samples

| SAMPLE ID | TISSUE | CANCER | MATCHING NORMAL ADJACENT |
|---|---|---|---|
| StoMT54 | Stomach 1 | 0 | 0 |
| SmI21XA | Small Intestine 1 | 0 | 0 |
| ClnMT38 | Colon-Splenic Flexture(M)1 | 0 | 2613.50 |
| ClnAS45 | Colon-Ascending(A)2 | 368.10 | 2129.40 |
| ClnCM67 | Colon-Cecum(B)3 | 6.87 | 545.36 |
| ClnB56 | Colon-Cecum(C)4 | 22.2 | 1089.90 |
| ClnAS67 | Colon-Ascending(B)5 | 0.3 | 147.0 |
| ClnAS12 | Colon-Ascending(B)6 | 55.59 | 1716.90 |
| ClnAS43 | Colon-Ascending(C)7 | 3.10 | 388.40 |
| ClnAS46 | Colon-Ascending(C)8 | 5.30 | 4582.20 |
| ClnAS89 | Colon-Ascending(D)9 | 43.00 | 291.00 |
| ClnAS98 | Colon-Ascending(C)10 | 34.1 | 5461.10 |
| ClnAC19 | Colon-Ascending(D)11 | 2.80 | 835.75 |
| ClnTX01 | Colon-Transverse(B)12 | 0.24 | 609.40 |
| ClnTX89 | Colon-Transverse(B)13 | 1.7 | 127.60 |
| ClnTX67 | Colon-Transverse(C)14 | 0.20 | 499.7 |
| ClnDC63 | Colon-Descending(C)15 | 53.50 | 1873.40 |
| ClnSG67 | Colon-Sigmoid(C)16 | 2.52 | 13.95 |
| ClnSG20 | Colon-Sigmoid(B)17 | 0.30 | 3381.54 |
| ClnSG45 | Colon-Sigmoid(D)18 | 6.70 | 1494.0 |
| ClnSG89 | Colon-Sigmoid(B)19 | 27.4 | 1441.40 |
| ClnSG36 | Colon-Sigmoid(B)20 | 2.7 | 4577.14 |
| ClnSG33 | Colon-Sigmoid(C)21 | 64.5 | 1320.98 |
| ClnSG20 | Colon-Sigmoid(B)22 | 0.3 | 3381.54 |
| ClnSG27 | Colon-Sigmoid(B)23 | 77.7 | 2739.50 |
| ClnSG66 | Colon-Sigmoid(C)24 | 0.1 | 1222.66 |
| ClnRC24 | Colon-Rectum(D)25 | 2292.2 | 3972.90 |
| ClnRC01 | Colon-Rectum(C)26 | 2267.9 | 33.08 |
| ClnCXGA | Colon-Rectum(A)27 | 1.10 | 1991.42 |
| ClnRC67 | Colon-Rectum(B)28 | 25.10 | 626.00 |

TABLE 4-continued

Relative Levels of GSG Cln115 Expression in Individual Samples

| SAMPLE ID | TISSUE | CANCER | MATCHING NORMAL ADJACENT |
|---|---|---|---|
| ClnSG98 | Colon-Rectosigmoid(C)29 | 42.46 | 1884.52 |
| ClnRS45 | Colon-Rectosigmoid(C)30 | 689.80 | 1567.79 |
| ClnRS16 | Colon-Rectosigmoid(B)31 | 286.51 | 1049.25 |
| ClnRS53 | Colon-Rectosigmoid(C)32 | 9.42 | 2529.61 |
| ClnB34 | Colon-Rectosigmoid(A)33 | 1.20 | 394.80 |
| ClnC9XR | Colon-Rectosigmoid(C)34 | 6.30 | 2741.70 |
| ClnDC19 | Colon-Descending(B)35 | 351.50 | 1197.10 |
| ClnDC22 | Colon-Descending(D)36 | 19.30 | 2576.20 |
| ClnRC01 | Colon-Rectum(C)37 | 1351.2 | 116.2 |
| ClnRC89 | Colon-Rectum(D)38 | 0.40 | 1024.0 |
| Bld32XK | Bladder 1 | 0.12 | 0.54 |
| CvxKS52 | Cervix 1 | 4.33 | 7.91 |
| End10479 | Endometrium 1 | 0 | 0 |
| Kid107XD | Kidney 1 | 0.84 | 9.62 |
| Kid109XD | Kidney 2 | 0 | 1.42 |
| Kid106XD | Kidney 3 | 0.28 | 0 |
| Liv15XA | Liver 1 | 1.00 | 0.41 |
| Lng47XQ | Lung 1 | 0 | 0 |
| Mam12X | Mammary Gland 1 | 0 | 0 |
| Tst39X | Testis 1 | 0 | 0 |
| Utr85XU | Uterus 1 | 0 | 0 |

0 = Negative

In the analysis of matching samples, the higher levels of expression were in colon. These results confirm the tissue specificity results obtained with normal pooled samples (Table 3).

Furthermore, the level of mRNA expression in cancer samples and the isogenic normal adjacent tissue from the same individual were compared. This comparison provides an indication of specificity for the cancer stage (e.g. lower levels of mRNA expression in the cancer sample compared to the normal adjacent). Table 4 shows lower expression of Cln115 in 36 colon cancer tissues compared with their respective normal adjacent out of a total of 38 matching samples tested. Thus, there is lower expression in the cancer tissue for 94.7% of the colon matching samples tested (total of 38 colon matching samples). The only cancer samples that showed overexpression of Cln115 were colon#26 and #37. After establishing a normal value for healthy individuals, lower levels of the product encoded by the gene Cln115 could have diagnostic value to determine the presence of colon cancer, detecting close to 94% of the cases tested.

Altogether, the high level of tissue specificity, plus the mRNA differential expression in the matching samples tested are indicative of Cln115 being a diagnostic marker for gastrointestinal cancer, and in particular colon cancer.

Example 2

Expression of Cln114 in *E. Coli*

Cln114 was amplified by polymerase chain reaction (PCR) using colon cDNA libraries and Cln specific primers. The amplified DNA fragment encoding amino acid number 1 ($Met^1$) to amino acid number 323 ($Ile^{323}$) of Cln114 was subcloned in a T7 RNA polymerase-based system (pET-21d) for expression in *E. coli*. In addition to Cln114 DNA coding sequence ($Met^1$-$Ile^{323}$), codons for six histidines, flanking the COOH-terminus of Cln114, were incorporated to use as purification tag.

Cln114 Construct: $Met^1$-$Ile^{323}$ $(His)_6$ $NH_2$/MAYVPAPGYQPTYNPTLPYYQPIPGGLNV-GMSVYIQGVASEHMKRFFVNFVVGQDPGSDVAFH-FNPRF DGWDKVVFNTLQGGKWGSEERKRSM-PFKKGAAFELVFIVLAEHYKVVVNGNPFYEYGHRL-PLQMVTHLQVD GDLQLQSINFIGGQPLRPQGPPMM-PPYPGPGHCHQQLNSLPTMEGPPTFNPPVPYFGRLQ-GGLTARRTIII KGYVPPTGKSFAINFKVGSSGDIAL-HINPRMGNGTVVRNSLLNGSWGSEEKKITHNPFGPG-QFFDLSIRCG LDRFKVYANGQHLFDFAHRL-SAFQRVDTLEIQGDVTLSYVQI<u>HHHHHH</u>/COOH (SEQ ID NO:13)

A high level of Cln114 expression was observed when the plasmid construct was transformed in *E. coli* host BL21-CODONPLUS(DE3). An over-expressed protein band of approximately 36 kDa was readily observed on a Coomassie blue stained polyacrylamide gel. Positive result from Western blot analysis using monoclonal antibody against 6xHistidine tag confirmed the expression of Cln114.

What is claimed is:

1. A method for detecting the presence of gastrointestinal cancer in a patient comprising:
   (a) determining levels of SEQ ID NO:3 or a polynucleotide encoding a polypeptide comprising SEQ ID NO:4 in cells, tissues or bodily fluids in a patient; and
   (b) comparing the determined levels of SEQ ID NO:3 or a polynucleotide encoding a polypeptide comprising SEQ ID NO:4 with levels of SEQ ID NO:3 or a polynucleotide encoding a polypeptide comprising SEQ ID NO:4 in cells, tissues or bodily fluids from a normal human control, wherein at least a two-fold decrease in determined levels of SEQ ID NO:3 or a polynucleotide encoding a polypeptide comprising SEQ ID NO:4 in said patient versus normal human control is associated with the presence of gastrointestinal cancer.

* * * * *

UNITED STATES PATENT AND TRADEMARK OFFICE
CERTIFICATE OF CORRECTION

| | |
|---|---|
| PATENT NO. | : 6,953,658 B2 |
| APPLICATION NO. | : 09/802674 |
| DATED | : October 11, 2005 |
| INVENTOR(S) | : Macina et al. |

Page 1 of 1

It is certified that error appears in the above-identified patent and that said Letters Patent is hereby corrected as shown below:

Title Page;

ON THE FACE OF THE PATENT: (75) Inventors: Please delete "Yongmng Sun" and insert --Yongming Sun--.

At column 7, line 56: Please delete "formulation" and insert --formylation--.

At column 12, line 59: Please delete "calorimetric" and insert --colorimetric--.

Signed and Sealed this

Twenty-seventh Day of November, 2007

JON W. DUDAS
*Director of the United States Patent and Trademark Office*

SEQUENCE LISTING

<160> NUMBER OF SEQ ID NOS: 13

<210> SEQ ID NO 1
<211> LENGTH: 1866
<212> TYPE: DNA
<213> ORGANISM: Homo sapiens

<400> SEQUENCE: 1

```
actcccctcc gagggtctg accacgcttg ggccgagtca tacgcccacg cgtccgggac      60
ctcctgccct caggtgatcc atccacctcg gccagtcaaa gtgctgggat tacaggcatg     120
agccattgca cccagccgat actactatat ccccatttta cagatgagca catgggcaaa     180
ttgagggtaa ggcactgacc catgatcata cagctgagaa gtggcaaagg caggatttga     240
acctagaacc tctggctcca cacactagta atctaaacca ctctccctac aatacaacat     300
acgtggtaaa gatgtgtggt gggcacgcaa tcaacgtagg tcccttcaca gttgctggga     360
gaggcaggaa tttgcagttc ctccgcgttc tcctcctccg ctgcccacct gtcctgggtc     420
```

-continued

```
attcctgcag cctgccctgc cctgcctggt ctcaccctcc ctctgccaac agaagtctgg   480
gcagggtttt atgggctctg ataaggccct ggcagggccg aagttcatga gcacttcctc   540
tttgcaggag ggcgtagggg agggaccca ggtgatttgg gtcctggctg gtcaccaggg    600
aagctggcaa gggaagggag actagggtgc gctctaggag aagccgacag cctgagagtc   660
ccagaagagg agccctgtgg accctcccct gccagccact cccttaccct gggtataaga   720
gccaccaccg cctgccatcc gccaccatct cccactcctg cagctcttct cacaggacca   780
gccactagcg cagcctcgag cgatggccta tgtccccgca ccgggctacc agcccaccta   840
caacccgacg ctgccttact accagcccat cccgggcggg ctcaacgtgg gaatgtctgt   900
ttacatccaa ggagtggcca gcgagcacat gaagcggttc ttcgtgaact ttgtggttgg   960
gcaggatccg ggctcagacg tcgccttcca cttcaatccg cggtttgacg gctgggacaa  1020
ggtggtcttc aacacgttgc agggcgggaa gtggggcagc gaggagagga agaggagcat  1080
gcccttcaaa aagggtgccg cctttgagct ggtcttcata gtcctggctg agcactacaa  1140
ggtggtggta atggaaatcc ccttctatga gtacgggcac cggcttcccc tacagatggt  1200
cacccacctg caagtggatg gggatctgca acttcaatca atcaacttca tcggaggcca  1260 gccctccgg cccagggac ccccgatgat gccaccttac cctggtcccg gacattgcca   1320
tcaacagctg aacagcctgc ccaccatgga aggaccccca accttcaacc cgcctgtgcc  1380
atatttcggg aggctgcaag gagggctcac agctcgaaga accatcatca tcaagggcta  1440
tgtgcctccc acaggcaaga gctttgctat caacttcaag gtgggctcct cagggacat   1500 agctctgcac attaatcccc gcatgggcaa cggtaccgtg gtccggaaca gccttctgaa  1560
tggctcgtgg ggatccgagg agaagaagat cacccacaac ccatttggtc ccggacagtt  1620
ctttgatctg tccattcgct gtggcttgga tcgcttcaag gtttacgcca atggccagca  1680 cctcttgac tttgcccatc gcctctcggc cttccagagg gtggacacat ggaaatcca   1740 gggtgatgtc accttgtcct atgtccagat ctaatctatt cctggggcca taactcatgg  1800
gaaaacagaa ttatccccta ggactccttt ctaagcccct aataaaatgt ctgagggtgt  1860
ctcatg                                                            1866
```

<210> SEQ ID NO 2
<211> LENGTH: 323
<212> TYPE: PRT
<213> ORGANISM: Homo sapiens

<400> SEQUENCE: 2

```
Met Ala Tyr Val Pro Ala Pro Gly Tyr Gln Pro Thr Tyr Asn Pro Thr
  1               5                  10                  15

Leu Pro Tyr Tyr Gln Pro Ile Pro Gly Gly Leu Asn Val Gly Met Ser
             20                  25                  30

Val Tyr Ile Gln Gly Val Ala Ser Glu His Met Lys Arg Phe Phe Val
         35                  40                  45

Asn Phe Val Val Gly Gln Asp Pro Gly Ser Asp Val Ala Phe His Phe
     50                  55                  60

Asn Pro Arg Phe Asp Gly Trp Asp Lys Val Val Phe Asn Thr Leu Gln
 65                  70                  75                  80

Gly Gly Lys Trp Gly Ser Glu Glu Arg Lys Arg Ser Met Pro Phe Lys
                 85                  90                  95

Lys Gly Ala Ala Phe Glu Leu Val Phe Ile Val Leu Ala Glu His Tyr
            100                 105                 110
```

-continued

Lys Val Val Asn Gly Asn Pro Phe Tyr Glu Tyr Gly His Arg Leu
            115                 120                 125

Pro Leu Gln Met Val Thr His Leu Gln Val Asp Gly Asp Leu Gln Leu
        130                 135                 140

Gln Ser Ile Asn Phe Ile Gly Gly Gln Pro Leu Arg Pro Gln Gly Pro
145                 150                 155                 160

Pro Met Met Pro Pro Tyr Pro Gly Pro Gly His Cys His Gln Gln Leu
                165                 170                 175

Asn Ser Leu Pro Thr Met Glu Gly Pro Pro Thr Phe Asn Pro Pro Val
            180                 185                 190

Pro Tyr Phe Gly Arg Leu Gln Gly Gly Leu Thr Ala Arg Arg Thr Ile
        195                 200                 205

Ile Ile Lys Gly Tyr Val Pro Pro Thr Gly Lys Ser Phe Ala Ile Asn
    210                 215                 220

Phe Lys Val Gly Ser Ser Gly Asp Ile Ala Leu His Ile Asn Pro Arg
225                 230                 235                 240

Met Gly Asn Gly Thr Val Val Arg Asn Ser Leu Leu Asn Gly Ser Trp
                245                 250                 255

Gly Ser Glu Glu Lys Lys Ile Thr His Asn Pro Phe Gly Pro Gly Gln
            260                 265                 270

Phe Phe Asp Leu Ser Ile Arg Cys Gly Leu Asp Arg Phe Lys Val Tyr
        275                 280                 285

Ala Asn Gly Gln His Leu Phe Asp Phe Ala His Arg Leu Ser Ala Phe
    290                 295                 300

Gln Arg Val Asp Thr Leu Glu Ile Gln Gly Asp Val Thr Leu Ser Tyr
305                 310                 315                 320

Val Gln Ile

<210> SEQ ID NO 3
<211> LENGTH: 2785
<212> TYPE: DNA
<213> ORGANISM: Homo sapiens

<400> SEQUENCE: 3
ctttagccca acagtcaaaa ataattgatg ctaccctaca aatgtccaaa actctagtat      60
atcatatttc taagttacag caaatattag tcctgctaaa ccagggagct ttggcaaaaa     120
tgttttttga cagtaaattt gtccttgatt atatattaac tagtcaaaga ggtgtttgta     180
acattattag agcttcttgt tgtaggtggg ttaacaccac caatcaagag gtcattctaa     240
cagaaagcct ggatcagaaa accatcaccc taaaaaaaca tgccttacat atttaacaca     300
ctctgaaatc cagtcaaaat atgactaaag gcccttgcca tgactgatgt attctcctgg     360
ccaacgccaa acaaatggga gcctggttac gagtcagcct tcagggactt gtcacatttc     420
tacttggttt cttccttgtt attgtcataa taaaatgttt tctatgctgt ttagtgcaac     480
ttaggcccta ttctgtagaa gtctcctcta ctattcaggc cactcaaaca ccccaaataa     540
ttgagttcaa aatcgacatc aagatataaa ggaatcagtg actaaatata tttcatatat     600
ggtatttta ttgattattg tgctgtcttg acctagtatg gaggccttgg ctagaggctg      660
gtcagtttcc tctcttgagc agctgattaa atccacaccc caaccacttc ccttatcagg     720
ttctcacact ctgggccac tatgtaccca ctctaatcac cacagggcca gacatcagac       780
aattaaggac agcgcccatg ccccaaagcc cgccaaaatt atgcaaatta ttcaaaatta     840
ttcaacctag ctaaccccac ccttttttgct gtacataagc tgcccattcc ccctccagcc     900

-continued

```
tgtggtaccc agtcctcagg tgcaacccca tgcgtggtcc tctgtggcag ccttctctca    960
ttcagagctg ttttccacag aggtagtgaa agaactgga ttttcaagtt cactttgcaa   1020
gagaaaaaga aaactcagta gaagataatg gcaagtccag actggggata tgatgacaaa   1080
aatggtcctg aacaatggag caagctgtat cccattgcca atggaaataa ccaatcccct   1140
gttgatatta aaaccagtga aaccaaacat gacacctctc tgaaacctat tagtgtctcc   1200
tacaacccag ccacagccaa agaaattatc aatgtggggc attctttcca tgtaaatttt   1260
gaggacaacg ataaccgatc agtgctgaaa ggtggtcctt tctctgacag ctacaggctc   1320
tttcagtttc attttcactg gggcagtaca aatgagcatg gttcagaaca tacagtggat   1380
ggagtcaaat attctgccga gcttcacgta gctcactgga attctgcaaa gtactccagc   1440
cttgctgaag ctgcctcaaa ggctgatggt ttggcagtta ttggtgtttt gatgaaggtt   1500
ggtgaggcca acccaaagct gcagaaagta cttgatgccc tccaagcaat taaaaccaag   1560
ggcaaacgag ccccattcac aaattttgac ccctctactc tccttccttc atccctggat   1620
ttctggacct accctggctc tctgactcat cctcctcttt atgagagtgt aacttggatc   1680
atctgtaagg agagcatcag tgtcagctca gagcagctgg cacaattccg cagccttcta   1740
tcaaatgttg aaggtgataa cgctgtcccc atgcagcaca caaccgccc aacccaacct   1800
ctgaagggca gaacagtgag agcttcattt tgatgattct gagaagaaac ttgtccttcc   1860
tcaagaacac agccctgctt ctgacataat ccagttaaaa taataatttt taagaaataa   1920
atttatttca atattagcaa gacagcatgc cttcaaatca atctgtaaaa ctaagaaact   1980
taaattttag ttcttactgc ttaattcaaa taataattag taagctagca aatagtaatc   2040
tgtaagcata agcttatctt aaattcaagt ttagtttgag gaattcttta aaattacaac   2100
taagtgattt gtatgtctat ttttttcagt ttatttgaac caataaaata attttatctc   2160
tttctttctg ttgtgcattc agtttctaaa accattaagt ttctactcca tttacattca   2220
aaaatcttaa atactttact tgcaagagta ttttgcttca aatacaacaa cctaagagca   2280
gctggagatg aaatattggg aaattcattt gcttactcct gaagacaaaa atatagctga   2340
gatgaccact ggatttaata tcgttatgct ggcccaacat tgctaccatt tgtgttgtct   2400
gtgatcaaaa tgattatctt ttatatagga agatgacgct tctggatatt gctttcactt   2460
cttctcccca cgttagcaag gacaatgctt ctctgccatt attacaacta gttagtttgc   2520
atggagaatc tttactttaa aattggaaga aaagtcacaa gtgaatggtt tataaaaatg   2580
ctaaagaagt cattcttgct tagaatcata tagaaacatc atgcaatctt ttagtcagat   2640
gtgcgcttca ccttatgcta ttttatctt taattgacac acaataattg tacatgttta   2700
tggagtatag tgtggtgttt tctgtttgtt tgtttgtttt ttgagacaag gtctcactct   2760
gccagtcagg gtggagtgcg atggt                                         2785
```

<210> SEQ ID NO 4
<211> LENGTH: 261
<212> TYPE: PRT
<213> ORGANISM: Homo sapiens

<400> SEQUENCE: 4

Met Ala Ser Pro Asp Trp Gly Tyr Asp Asp Lys Asn Gly Pro Glu Gln
 1               5                  10                  15

Trp Ser Lys Leu Tyr Pro Ile Ala Asn Gly Asn Asn Gln Ser Pro Val
            20                  25                  30

```
Asp Ile Lys Thr Ser Glu Thr Lys His Asp Thr Ser Leu Lys Pro Ile
             35                  40                  45
Ser Val Ser Tyr Asn Pro Ala Thr Ala Lys Glu Ile Ile Asn Val Gly
         50                  55                  60
His Ser Phe His Val Asn Phe Glu Asp Asn Asp Asn Arg Ser Val Leu
 65                  70                  75                  80
Lys Gly Gly Pro Phe Ser Asp Ser Tyr Arg Leu Phe Gln Phe His Phe
                 85                  90                  95
His Trp Gly Ser Thr Asn Glu His Gly Ser Glu His Thr Val Asp Gly
            100                 105                 110
Val Lys Tyr Ser Ala Glu Leu His Val Ala His Trp Asn Ser Ala Lys
        115                 120                 125
Tyr Ser Ser Leu Ala Glu Ala Ala Ser Lys Ala Asp Gly Leu Ala Val
    130                 135                 140
Ile Gly Val Leu Met Lys Val Gly Glu Ala Asn Pro Lys Leu Gln Lys
145                 150                 155                 160
Val Leu Asp Ala Leu Gln Ala Ile Lys Thr Lys Gly Lys Arg Ala Pro
                165                 170                 175
Phe Thr Asn Phe Asp Pro Ser Thr Leu Leu Pro Ser Ser Leu Asp Phe
            180                 185                 190
Trp Thr Tyr Pro Gly Ser Leu Thr His Pro Pro Leu Tyr Glu Ser Val
        195                 200                 205
Thr Trp Ile Ile Cys Lys Glu Ser Ile Ser Val Ser Ser Glu Gln Leu
    210                 215                 220
Ala Gln Phe Arg Ser Leu Leu Ser Asn Val Glu Gly Asp Asn Ala Val
225                 230                 235                 240
Pro Met Gln His Asn Asn Arg Pro Thr Gln Pro Leu Lys Gly Arg Thr
                245                 250                 255
Val Arg Ala Ser Phe
            260

<210> SEQ ID NO 5
<211> LENGTH: 18
<212> TYPE: PRT
<213> ORGANISM: Homo sapiens

<400> SEQUENCE: 5

Pro Ala Pro Gly Tyr Gln Pro Thr Tyr Asn Pro Thr Leu Pro Tyr Tyr
 1               5                  10                  15
Gln Pro

<210> SEQ ID NO 6
<211> LENGTH: 26
<212> TYPE: PRT
<213> ORGANISM: Homo sapiens

<400> SEQUENCE: 6

Pro Arg Phe Asp Gly Trp Asp Lys Val Val Phe Asn Thr Leu Gln Gly
 1               5                  10                  15
Gly Lys Trp Gly Ser Glu Glu Arg Lys Arg
            20                  25

<210> SEQ ID NO 7
<211> LENGTH: 24
<212> TYPE: PRT
<213> ORGANISM: Homo sapiens

<400> SEQUENCE: 7
```

-continued

Pro Leu Arg Pro Gln Gly Pro Pro Met Met Pro Pro Tyr Pro Gly Pro
1               5                   10                  15

Gly His Cys His Gln Gln Leu Asn
            20

<210> SEQ ID NO 8
<211> LENGTH: 15
<212> TYPE: PRT
<213> ORGANISM: Homo sapiens

<400> SEQUENCE: 8

Trp Gly Ser Glu Glu Lys Lys Ile Thr His Asn Pro Phe Gly Pro
1               5                   10                  15

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 9
aacccgcctg tgccatatt                                            19

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 10
ggagcccacc ttgaagttga ta                                        22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 11
ggctgatggt ttggcagtta                                           20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 12
ttgtgaatgg ggctcgttt                                            19

<210> SEQ ID NO 13
<211> LENGTH: 329
<212> TYPE: PRT
<213> ORGANISM: Homo sapiens

<400> SEQUENCE: 13

Met Ala Tyr Val Pro Ala Pro Gly Tyr Gln Pro Thr Tyr Asn Pro Thr
1               5                   10                  15

Leu Pro Tyr Tyr Gln Pro Ile Pro Gly Gly Leu Asn Val Gly Met Ser
            20                  25                  30

-continued

```
Val Tyr Ile Gln Gly Val Ala Ser Glu His Met Lys Arg Phe Phe Val
        35                  40                  45

Asn Phe Val Val Gly Gln Asp Pro Gly Ser Asp Val Ala Phe His Phe
        50                  55                  60

Asn Pro Arg Phe Asp Gly Trp Asp Lys Val Val Phe Asn Thr Leu Gln
65                  70                  75                  80

Gly Gly Lys Trp Gly Ser Glu Glu Arg Lys Arg Ser Met Pro Phe Lys
                85                  90                  95

Lys Gly Ala Ala Phe Glu Leu Val Phe Ile Val Leu Ala Glu His Tyr
                100                 105                 110

Lys Val Val Asn Gly Asn Pro Phe Tyr Glu Tyr Gly His Arg Leu
        115                 120                 125

Pro Leu Gln Met Val Thr His Leu Gln Val Asp Gly Asp Leu Gln Leu
        130                 135                 140

Gln Ser Ile Asn Phe Ile Gly Gly Gln Pro Leu Arg Pro Gln Gly Pro
145                 150                 155                 160

Pro Met Met Pro Pro Tyr Pro Gly Pro Gly His Cys His Gln Gln Leu
                165                 170                 175

Asn Ser Leu Pro Thr Met Glu Gly Pro Pro Thr Phe Asn Pro Pro Val
                180                 185                 190

Pro Tyr Phe Gly Arg Leu Gln Gly Gly Leu Thr Ala Arg Arg Thr Ile
        195                 200                 205

Ile Ile Lys Gly Tyr Val Pro Pro Thr Gly Lys Ser Phe Ala Ile Asn
        210                 215                 220

Phe Lys Val Gly Ser Ser Gly Asp Ile Ala Leu His Ile Asn Pro Arg
225                 230                 235                 240

Met Gly Asn Gly Thr Val Val Arg Asn Ser Leu Leu Asn Gly Ser Trp
                245                 250                 255

Gly Ser Glu Glu Lys Lys Ile Thr His Asn Pro Phe Gly Pro Gly Gln
                260                 265                 270

Phe Phe Asp Leu Ser Ile Arg Cys Gly Leu Asp Arg Phe Lys Val Tyr
        275                 280                 285

Ala Asn Gly Gln His Leu Phe Asp Phe Ala His Arg Leu Ser Ala Phe
        290                 295                 300

Gln Arg Val Asp Thr Leu Glu Ile Gln Gly Asp Val Thr Leu Ser Tyr
305                 310                 315                 320

Val Gln Ile His His His His His His
                325
```